US008382803B2

(12) United States Patent
Schmocker

(10) Patent No.: US 8,382,803 B2
(45) Date of Patent: Feb. 26, 2013

(54) VERTEBRAL STABILIZATION TRANSITION CONNECTOR

(75) Inventor: Sonia Schmocker, Romanshorn (CH)

(73) Assignee: Zimmer GmbH, Winterthur (CH)

( * ) Notice: Subject to any disclaimer, the term of this patent is extended or adjusted under 35 U.S.C. 154(b) by 130 days.

(21) Appl. No.: 12/871,569

(22) Filed: Aug. 30, 2010

(65) Prior Publication Data

US 2012/0053636 A1    Mar. 1, 2012

(51) Int. Cl.
*A61B 17/70* (2006.01)

(52) U.S. Cl. ......... 606/260; 606/259; 606/264; 606/278

(58) Field of Classification Search .......... 606/250–278; 403/307; 411/389, 436
See application file for complete search history.

(56) References Cited

U.S. PATENT DOCUMENTS

| | | | |
|---|---|---|---|
| 1,953,095 A * | 4/1934 | Baker | 403/307 |
| 4,743,260 A | 5/1988 | Burton | |
| 5,176,708 A | 1/1993 | Frey et al. | |
| 5,375,823 A | 12/1994 | Navas | |
| 5,540,688 A | 7/1996 | Navas | |
| 5,562,660 A | 10/1996 | Grob | |
| 5,725,582 A | 3/1998 | Bevan et al. | |
| 5,782,831 A | 7/1998 | Sherman et al. | |
| RE36,221 E | 6/1999 | Breard et al. | |
| 5,997,542 A * | 12/1999 | Burke | 606/74 |
| 6,248,106 B1 | 6/2001 | Ferree | |
| 6,290,700 B1 | 9/2001 | Schmotzer | |
| 6,610,079 B1 | 8/2003 | Li et al. | |
| 6,802,844 B2 | 10/2004 | Ferree | |
| 6,880,224 B2 * | 4/2005 | Colarusso et al. | 29/456 |
| 6,986,771 B2 | 1/2006 | Paul et al. | |
| 6,989,011 B2 | 1/2006 | Paul et al. | |
| 7,029,475 B2 | 4/2006 | Panjabi | |
| 7,137,985 B2 | 11/2006 | Jahng | |
| 7,326,210 B2 | 2/2008 | Jahng et al. | |
| 7,641,673 B2 | 1/2010 | Le Couedic et al. | |
| 7,985,041 B2 * | 7/2011 | Lin | 411/427 |
| 8,097,022 B2 * | 1/2012 | Marik | 606/260 |
| 2002/0035366 A1 | 3/2002 | Walder et al. | |
| 2003/0220643 A1 | 11/2003 | Ferree | |
| 2004/0049189 A1 | 3/2004 | Le Couedic et al. | |
| 2004/0215190 A1 * | 10/2004 | Nguyen et al. | 606/61 |
| 2004/0215191 A1 | 10/2004 | Kitchen | |

(Continued)

FOREIGN PATENT DOCUMENTS

| | | |
|---|---|---|
| EP | 0669109 B1 | 5/1999 |
| EP | 0669109 A1 | 8/1999 |

(Continued)

OTHER PUBLICATIONS

Davis et al., "The Dynamic Stabilization System", Zimmer Spine, Inc. 2005.

*Primary Examiner* — Jan Christopher Merene

(74) *Attorney, Agent, or Firm* — Seager Tufte & Wickhem LLC

(57) ABSTRACT

A transition connector of a vertebral stabilization system for connecting a rigid rod and a flexible member to provide regions of rigid support and regions of dynamic support along a region of the spinal column is disclosed. A rigid rod may form one portion of the transition connector and a tubular member configured to receive a flexible member may form another portion of the transition connector. The tubular member may be configured to be secured to an end portion of the flexible member.

15 Claims, 15 Drawing Sheets

U.S. PATENT DOCUMENTS

| | | | |
|---|---|---|---|
| 2004/0225289 A1 | 11/2004 | Biedermann et al. | |
| 2004/0261244 A1* | 12/2004 | Colarusso et al. | 29/456 |
| 2005/0010220 A1 | 1/2005 | Casutt et al. | |
| 2005/0056979 A1 | 3/2005 | Studer et al. | |
| 2005/0065416 A1 | 3/2005 | Subotics | |
| 2005/0085815 A1 | 4/2005 | Harms et al. | |
| 2005/0096652 A1 | 5/2005 | Burton | |
| 2005/0124991 A1 | 6/2005 | Jahng | |
| 2005/0143737 A1 | 6/2005 | Pafford et al. | |
| 2005/0154390 A1 | 7/2005 | Biedermann et al. | |
| 2005/0177157 A1 | 8/2005 | Jahng | |
| 2005/0203511 A1 | 9/2005 | Wilson-MacDonald et al. | |
| 2005/0203513 A1 | 9/2005 | Jahng et al. | |
| 2005/0203514 A1 | 9/2005 | Jahng et al. | |
| 2005/0203517 A1 | 9/2005 | Jahng et al. | |
| 2005/0277922 A1 | 12/2005 | Trieu et al. | |
| 2006/0106380 A1 | 5/2006 | Colleran et al. | |
| 2006/0106381 A1 | 5/2006 | Ferree et al. | |
| 2006/0111715 A1 | 5/2006 | Jackson | |
| 2006/0142758 A1 | 6/2006 | Petit | |
| 2006/0173454 A1 | 8/2006 | Spitler et al. | |
| 2006/0195093 A1 | 8/2006 | Jahng | |
| 2006/0200129 A1 | 9/2006 | Denti | |
| 2006/0212033 A1 | 9/2006 | Rothman et al. | |
| 2006/0229611 A1* | 10/2006 | Avery et al. | 606/61 |
| 2006/0229615 A1 | 10/2006 | Abdou | |
| 2006/0247627 A1* | 11/2006 | Farris | 606/61 |
| 2006/0247638 A1 | 11/2006 | Trieu et al. | |
| 2007/0005062 A1 | 1/2007 | Lange et al. | |
| 2007/0005063 A1 | 1/2007 | Bruneau et al. | |
| 2007/0016200 A1 | 1/2007 | Jackson | |
| 2007/0055244 A1 | 3/2007 | Jackson | |
| 2007/0100341 A1 | 5/2007 | Reglos et al. | |
| 2007/0118119 A1 | 5/2007 | Hestad | |
| 2007/0129729 A1 | 6/2007 | Petit et al. | |
| 2007/0173825 A1* | 7/2007 | Sharifi-Mehr et al. | 606/61 |
| 2007/0198088 A1 | 8/2007 | Biedermann et al. | |
| 2007/0225710 A1 | 9/2007 | Jahng et al. | |
| 2007/0233075 A1 | 10/2007 | Dawson | |
| 2007/0233087 A1 | 10/2007 | Schlapfer | |
| 2007/0233095 A1 | 10/2007 | Schapfer | |
| 2007/0239158 A1 | 10/2007 | Trieu et al. | |
| 2007/0270821 A1 | 11/2007 | Trieu et al. | |
| 2007/0270860 A1 | 11/2007 | Jackson | |
| 2007/0293862 A1 | 12/2007 | Jackson | |
| 2008/0009863 A1 | 1/2008 | Bond et al. | |
| 2008/0021459 A1 | 1/2008 | Lim | |
| 2008/0021465 A1 | 1/2008 | Shadduck et al. | |
| 2008/0039843 A1 | 2/2008 | Abdou | |
| 2008/0045951 A1* | 2/2008 | Fanger et al. | 606/61 |
| 2008/0051787 A1 | 2/2008 | Remington et al. | |
| 2008/0091213 A1 | 4/2008 | Jackson | |
| 2008/0140076 A1 | 6/2008 | Jackson | |
| 2008/0140133 A1 | 6/2008 | Allard et al. | |
| 2008/0147122 A1 | 6/2008 | Jackson | |
| 2008/0161857 A1 | 7/2008 | Hestad et al. | |
| 2008/0177317 A1 | 7/2008 | Jackson | |
| 2008/0177388 A1* | 7/2008 | Patterson et al. | 623/17.16 |
| 2008/0183216 A1 | 7/2008 | Jackson | |
| 2008/0195153 A1 | 8/2008 | Thompson | |
| 2008/0234737 A1 | 9/2008 | Boschert | |
| 2008/0234738 A1 | 9/2008 | Zylber et al. | |
| 2008/0234744 A1 | 9/2008 | Zylber et al. | |
| 2008/0262551 A1 | 10/2008 | Rice et al. | |
| 2008/0275456 A1 | 11/2008 | Vonwiller et al. | |
| 2008/0294198 A1 | 11/2008 | Jackson | |
| 2008/0300633 A1 | 12/2008 | Jackson | |
| 2008/0319486 A1 | 12/2008 | Hestad et al. | |
| 2009/0005817 A1 | 1/2009 | Friedrich et al. | |
| 2009/0012562 A1 | 1/2009 | Hestad et al. | |
| 2009/0030464 A1 | 1/2009 | Hestad et al. | |
| 2009/0036924 A1 | 2/2009 | Egli et al. | |
| 2009/0082815 A1 | 3/2009 | Zylber et al. | |
| 2009/0093845 A1 | 4/2009 | Hestad et al. | |
| 2009/0093846 A1 | 4/2009 | Hestad | |
| 2009/0099606 A1 | 4/2009 | Hestad et al. | |
| 2009/0112265 A1 | 4/2009 | Hudgins et al. | |
| 2009/0118767 A1 | 5/2009 | Hestad et al. | |
| 2009/0198281 A1 | 8/2009 | Rice et al. | |
| 2009/0216281 A1 | 8/2009 | Vonwiller et al. | |
| 2010/0114167 A1* | 5/2010 | Wilcox et al. | 606/250 |
| 2010/0331887 A1 | 12/2010 | Jackson et al. | |

FOREIGN PATENT DOCUMENTS

| | | |
|---|---|---|
| EP | 1523949 A1 | 4/2005 |
| EP | 1523949 B1 | 6/2007 |
| FR | 2715057 | 7/1995 |
| FR | 2775583 | 9/1999 |
| FR | 2844180 | 3/2004 |
| FR | 2867057 | 9/2005 |
| NL | 7610576 | 9/1976 |
| WO | WO9519149 | 7/1995 |
| WO | WO9905980 | 2/1999 |
| WO | WO9944527 | 9/1999 |
| WO | WO 2004024011 | 3/2004 |
| WO | WO 2004089244 | 10/2004 |
| WO | WO 2005037110 | 4/2005 |
| WO | WO 2005037150 | 4/2005 |
| WO | WO 2005087121 | 9/2005 |
| WO | WO 2006066685 | 6/2006 |
| WO | WO 2007044795 | 4/2007 |
| WO | WO 2007087476 | 8/2007 |
| WO | WO 2008006098 | 1/2008 |
| WO | WO 2008013892 | 1/2008 |
| WO | WO 2008021319 | 2/2008 |
| WO | WO 2008034130 | 3/2008 |
| WO | WO 2008134703 | 11/2008 |

* cited by examiner

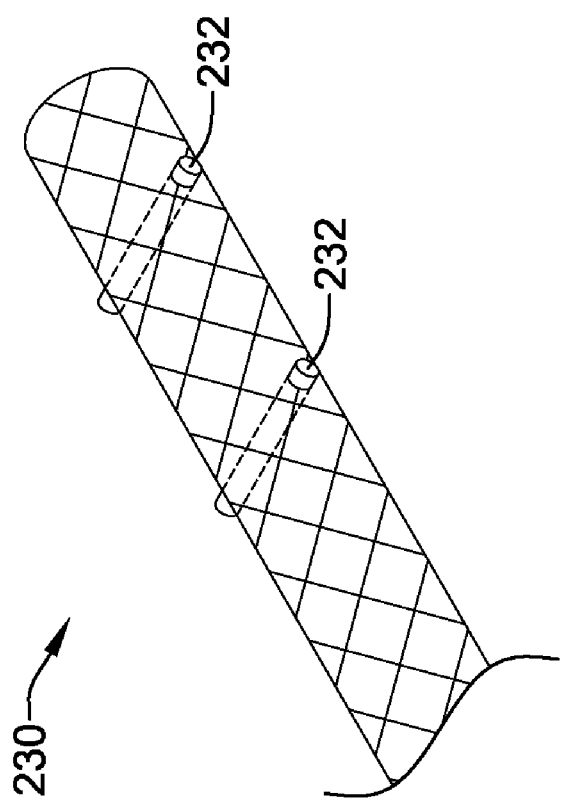

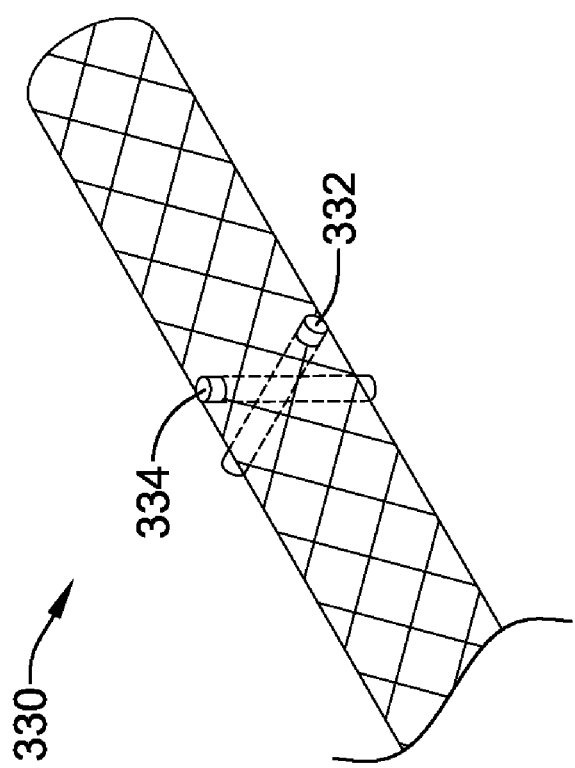

VERTEBRAL STABILIZATION TRANSITION CONNECTOR

TECHNICAL FIELD

The disclosure is directed to a system, apparatus and method for providing stabilization to one or more vertebrae of a spinal column. More particularly, the disclosure is directed to a system, apparatus and method for providing dynamic stability or support to one or more spinal segments of a spinal column.

BACKGROUND

The spinal column is a highly complex system of bones and connective tissues that provides support for the body and protects the delicate spinal cord and nerves. The spinal column includes a series of vertebrae stacked one on top of the other, each vertebra includes a vertebral body including an inner or central portion of relatively weak cancellous bone and an outer portion of relatively strong cortical bone. An intervertebral disc is situated between each vertebral body to cushion and dampen compressive forces experienced by the spinal column. A vertebral canal, called the foramen, containing the spinal cord and nerves is located posterior to the vertebral bodies. In spite of the complexities, the spine is a highly flexible structure, capable of a high degree of curvature and twist in nearly every direction. For example, the kinematics of the spine normally includes flexion, extension, rotation and lateral bending.

There are many types of spinal column disorders including scoliosis (abnormal curvature and twisting of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal disorders may also threaten the critical elements of the nervous system housed within the spinal column.

One particular spinal fixation technique includes immobilizing portions of the spine of a patient by using connecting elements such as relatively rigid orthopedic spine rods that run generally parallel to the spine. Another technique utilizes less rigid connecting elements to provide a more dynamic stabilization of the affected regions of the spine. One example of such a spinal stabilization system is the Dynesys® system available from, Zimmer Spine, Inc., of Minneapolis, Minn.

Installation of such systems may be accomplished, for example, by accessing the spine posteriorly and fastening hooks, bone screws, or other types of vertebral anchors to the pedicles or other bony structures of the appropriate vertebrae. The vertebral anchors may be generally placed in a quantity of two per vertebra, one on either side of the spinal cord, and serve as anchor points for the connecting elements.

It may be desirable for some spinal stabilization systems to have regions of more rigid stabilization and regions of more flexible stabilization. Accordingly, there is an ongoing need to provide alternative apparatus, devices, assemblies, systems and/or methods that can function to alleviate pain or discomfort, provide stability, such as dynamic stability, and/or restore a range of motion to a spinal segment of a spinal column.

SUMMARY

The disclosure is directed to several alternative designs, materials and methods of manufacturing spinal fixation hardware, structures, and assemblies. Some embodiments of the disclosure are directed to a spinal fixation assembly for affixing a flexible member, to a connector, along a region of the spinal column with a plurality of fasteners. In some embodiments, the flexible member may have an end portion and a reduced diameter portion extending from the end portion. The transition connector may have a first end and a second end with a lumen extending therebetween. The lumen may be configured to receive at least a portion of the flexible member. The lumen of the transition connector may be sized to engage the end portion of the flexible member and prevent the end portion of the flexible member from being removed from the lumen while the reduced diameter portion extends from the lumen.

Another embodiment is a vertebral stabilization system including a flexible member connected to a rigid rod through a transition connector. The flexible member may include an end portion having a first diameter and a reduced diameter portion extending from the end portion and having a second diameter. The transition connector may have a first end and a second end with a lumen extending therebetween. The lumen of the transition connector may taper from a larger diameter proximate the second end to a smaller diameter proximate the first end. The end portion of the flexible member may be disposed in the lumen of the transition connector such that the reduced diameter portion of the flexible member extends from the first end of the connector, Another embodiment is a spinal fixation assembly for affixing a flexible member, to a connector. The flexible member may include a first pin extending radially through a diameter of the flexible member such that a first end portion and a second end portion of the pin extend radially from the flexible member. The transition connector may have a first end and a second end and define a channel therebetween. The channel may be configured to receive the end portion of the flexible member. The transition connector may further include a plurality of slots formed in a sidewall of the channel. The end portion of the flexible member may be disposed in the channel such that the flexible member extends from the first end of the connector and the end portions of the pin are received in the slots.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 4A is a perspective view of an illustrative flexible member for assembly with the transition connector of FIG. 4;

FIG. 6A is a perspective view of an illustrative flexible member for assembly with the transition connector of FIG. 6;

Figure 1:
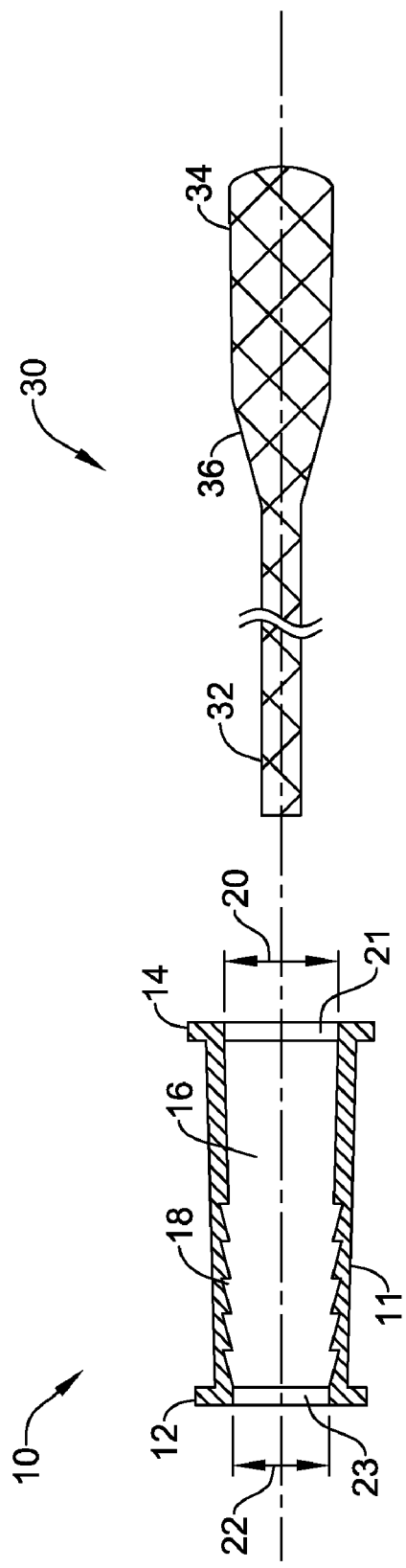
FIG. 1 is an axial cross-section of an illustrative transition connector and flexible member in an unassembled state.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the terms "vertebral stabilization system", "vertebral stabilization construct" and similar terms encompass any type of construct extending between adjacent vertebrae regardless of its rigidity, flexibility or construction.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now referring to the drawings, FIG. 1 is a cross-sectional view of an illustrative transition connector 10 for connecting a rigid rod construct and a flexible construct, to control relative motion of adjacent vertebrae along a region of a spinal column with a plurality of fasteners. In some embodiments, the flexible construct may be similar to the flexible cord of a vertebral stabilization system, as in the Dynesys® system offered by Zimmer Spine, Inc., of Minneapolis, Minn. For example, the transition connector 10 may connect a rigid rod to a flexible member such as a flexible cord. The transition connector 10 may allow for a rigid spinal stabilization system to transition to a more flexible spinal stabilization system. The transition connector 10 may be used in conjunction with one or more vertebral fasteners, such as bone screws, as will be described in more detail below. The transition connector 10 may be formed from any biocompatible material, such as, but not limited to, titanium or stainless steel, or a suitable polymeric material.

The transition connector 10 may include a rigid tubular member 11 having a first end 12 and a second end 14. The tubular member 11 may further include a lumen 16 extending from an opening 23 in the first end 12 to an opening 21 in the second end 14. In some instances, the first and second ends 12, 14 may include flange portions such that ends 12, 14 have an enlarged diameter portion relative to a middle portion of the tubular member 11. In some instances, the flange portions of ends 12, 14, may help retain transition connector 10 within the channel of a housing of a bone screw or other fixation device. In some embodiments, the tubular member 11 may have a uniform outer cross-sectional diameter along the length of the tubular member 11. In other embodiments, the first and second ends 12, 14 may have a smaller cross-sectional diameter than a middle portion of the tubular member 11. While transition connector 10 is shown as having a circular cross section, the transition connector 10 may have a cross section of any desired shape, including, but not limited to: square, rectangular, polygonal, or elliptical.

In some instances, at least a portion of the lumen 16 may be shaped to receive the end portion of a flexible cord 30 or other flexible member therein. While the lumen 16 is shown as having a generally circular shape, the lumen 16 may be of any shape desired to accommodate any shaped cord or other flexible member such as, but not limited to, square, rectangular, polygonal, or elliptical. The inner diameter or cross-sectional dimension of the lumen 16 may be substantially the same as or smaller than an outer diameter or cross sectional dimension of an enlarged end portion 34 of the flexible cord 30 or other flexible member.

In some embodiments, the rigid tubular member 11 may have a slightly conical shape. For example, in some instances, the outer diameter and/or the inner diameter may include a slight taper between the first end 12 and the second end 14. As illustrated, the lumen 16 may have a first diameter 22 proximate first end 12 and a second diameter 20 proximate second end 14. In some embodiments, second diameter 20 may be larger than first diameter 22. However, in some instances, second diameter 20 may be smaller than or substantially the same size as first diameter 22. The smaller diameter 22 portion may provide a compressive force on the enlarged diameter end portion 34 of the flexible cord 30 inserted into the lumen 16.

In some embodiments, the opening 23 at the first end 12 may have a diameter of about 3.5 mm, whereas the opening 21 at the second end 14 may have a diameter of about 4.1 mm. In other embodiments, the opening 23 at the first end 12 may have a diameter of about 3.5 mm, whereas the opening 21 at the second end 14 may have a diameter of about 5.5 mm. In other instances, the opening 23 at the first end 12 may have another diameter suitable for passing the reduced diameter portion 32 of the flexible cord 30 therethrough, yet not allowing the enlarged diameter portion 34 of the flexible cord 30 to pass through. With the diameter of the opening 21 sized larger than the diameter of the opening 23, the lumen 16 may taper from the diameter of the second opening 21 down to the diameter of the first opening 23.

Lumen 16 may further include one or more directional threads 18 or other retention features, such as ridges, grooves, teeth, surface roughenings, etc., disposed adjacent to the reduced diameter 22 end. The threads 18 may be configured such that once cord 30 has been slid into the lumen 16, the cord 30 cannot be pulled in the opposite direction. For example, threads 18 may grip or "bite" into a portion of the cord 30 that has a larger diameter than the lumen 16, as will be discussed in more detail below.

In one embodiment, the flexible cord 30 may be formed from polyethylene-terephthalate (PET), although it will be recognized that various other materials suitable for implantation within the human body and for providing stabilization of the spine while maintaining flexibility may be used. In other embodiments, the flexible cord 30 can be constructed of other flexible materials such as metal, polymeric materials, or combinations of flexible materials. The flexible cord 30 may be of any length necessary to extend between two, three, four, or more vertebrae of the spinal column.

Flexible cord 30 may have an end portion 34 having a first diameter and a reduced diameter portion 32 extending from the end portion 34 having a second diameter. The diameter of the reduced diameter portion 32 may be smaller than the diameter of the end portion 34. For example, in some instances, the diameter of the reduced diameter portion 32 may be smaller than the diameter of the lumen 16 while the end portion 34 may be larger than the diameter of at least a portion of the lumen 16. This may allow the reduced diameter portion 32 of the flexible cord 30 to easily pass through the lumen 16 of the transition connector 10 and out the opening 23. In some instances the diameter of the end portion 34 may be substantially the same as or larger than an inner diameter or cross sectional dimension of the lumen 16.

The diameter of the opening 21 may be sized larger than the diameters of the reduced diameter portion 32 and the enlarged diameter end portion 34 of the cord 30, whereas the diameter of the opening 23 may be sized larger than the diameter of the reduced diameter portion 32 of the cord 30, but smaller than the diameter of the enlarged diameter end portion 34 of the cord 30.

Flexible cord 30 may further include a transition region 36 between reduced diameter portion 32 and end portion 34. Transition region 36 may provide a gradual transition from the first diameter to the second diameter in the form of a taper or, alternatively, transition region 36 may be a step-wise transition in which the reduced diameter portion 32 directly transitions into the end portion 34. However, it is contemplated that in some embodiments, flexible cord 30 may have a constant diameter over the length of the cord 30.

In some embodiments, flexible cord 30 may be placed within the lumen 16 of the transition connector 10 from the second end 14. For example, reduced diameter end portion 32 of the cord 30 may be fed into the lumen 16 through the opening 21 at the second (larger) end 14 of the connector 10. Reduced diameter portion 32 may be pulled through the lumen 16 such that it exits the lumen 16 through the opening 23 at the first (smaller) end 12 of the connector 10. Thus, cord 30 may be pulled through the lumen 16 such that the reduced diameter portion 32 exits the lumen 16 while the enlarged diameter end portion 34 remains within the lumen 16. A cord tensioner, or other such device, may be used to pull the cord 30 through the lumen 16. The cord 30 may be pulled until the end portion 34 engages the inner surface of the lumen 16 and/or the reduced diameter 22 portion adjacent the first end 12 of the connector 10. As the cord 30 is slid through the lumen 16, the end portion 34 of the cord 30 may be compressed against the inner surface of the lumen 16 and reduced diameter 22 of the first end 12 of the connector 10. Retention features, such as threads 18 may engage the end portion 34 to help retain the end portion 34 in the lumen 16. As discussed above, threads 18 may be directional such that the cord 30 cannot be pulled out of the lumen 16 through the second (larger) end 14 of the connector 10.

A rigid rod (not shown) may be secured to and/or extend from the second end 14 of the connector 10. The rigid rod may have any length necessary to extend between two, three, four, or more vertebrae of the spinal column.

Although not illustrated, the reduced diameter portion 32 of the flexible member such as the flexible cord 30 may extending through a spacer, as well as other components if desired. In some embodiments, the spacer may be an annular spacer having a lumen extending from a first end to a second end of the spacer. For example, in some embodiments the spacer may be a cylindrical member having a lumen extending therethrough. In some embodiments, the spacer may be formed from polycarbonate urethane (PCU), although it will be recognized that various other materials suitable for implantation within the human body and for providing stabilization of the spine while maintaining flexibility may be used. In other embodiments, the spacer can be constructed of other materials such as metal, polymeric materials, or combinations of materials.

Figure 2:
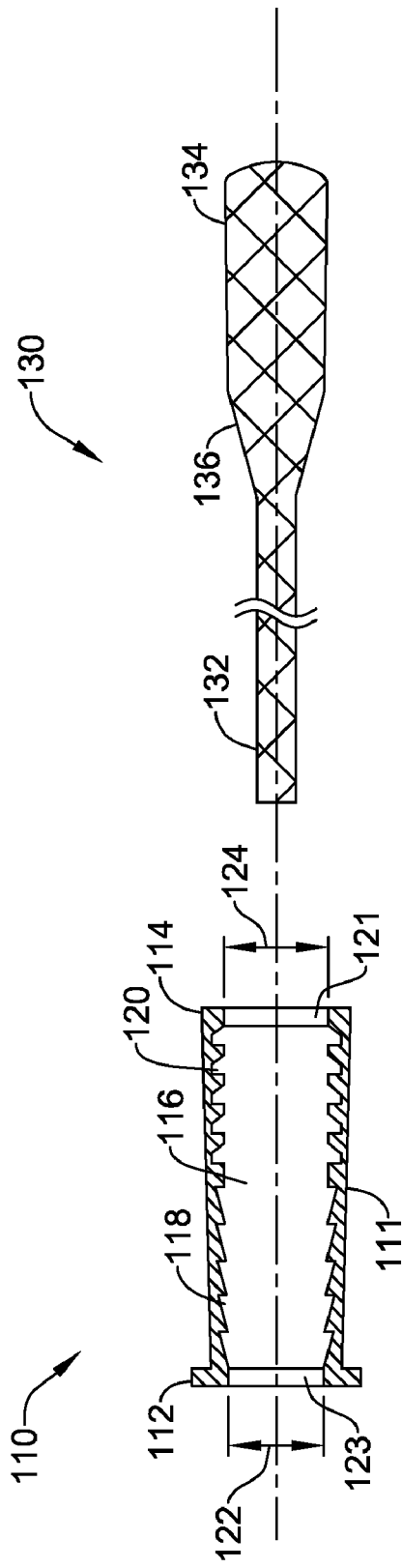
FIG. 2 is an axial cross-section of another illustrative transition connector and flexible member in an unassembled state.

FIG. 2 is a cross-sectional view of another illustrative transition connector 110 for connecting a rigid rod construct and a flexible construct, to control relative motion of adjacent vertebrae along a region of a spinal column with a plurality of fasteners, such as bone screws. The transition connector 110 may include a rigid tubular member 111 having a first end 112 and a second end 114. The tubular member 111 may further include a lumen 116 extending from an opening 123 in the first end 112 to an opening 121 in the second end 114. In some instances, the first and second ends 112, 114 may include flange portions such that ends 112, 114 have an enlarged diameter portion relative to a middle portion of the tubular member 111. In some instances, the flange portions of ends 112, 114, may help retain transition connector 110 within the housing of a pedicle screw or other fixation device. However, in some instances, it is contemplated that only one end may have a flange portion (e.g., first end 112 in FIG. 2). In some embodiments, the tubular member 111 may have a uniform outer cross-sectional diameter along the length of the tubular member 111. In other embodiments, the first and second ends 112, 114 may have a smaller cross-sectional diameter than a middle portion of the tubular member 111. While transition connector 110 is shown as having a circular cross section, the transition connector 110 may have a cross section of any desired shape, including, but not limited to: square, rectangular, polygonal, or elliptical.

In some instances, at least a portion of the lumen 116 may be shaped to receive the end portion of a flexible cord 130 or other flexible member therein. While the lumen 116 is shown as having a generally circular shape, the lumen 116 may be of any shape desired to accommodate any shaped cord or other flexible member such as, but not limited to, square, rectangular, polygonal, or elliptical. The inner diameter or cross-sectional dimension of the lumen 116 may be substantially the same as or smaller than an outer diameter or cross sectional dimension of an enlarged end portion 134 of the flexible cord 130 or other flexible member.

In some embodiments, the rigid tubular member 111 may have a slightly conical shape. For example, in some instances, the outer diameter and/or the inner diameter may include a slight taper between the first end 112 and the second end 114. As illustrated, the lumen 116 may have a first diameter 122 proximate first end 112 and a second diameter 124 proximate second end 114. In some embodiments, second diameter 124 may be larger than first diameter 122. However, in some instances, second diameter 124 may be smaller than or substantially the same size as first diameter 122. The smaller diameter 122 portion may provide a compressive force on the enlarged diameter end portion 134 of the flexible cord 130 inserted into the lumen 116.

In some embodiments, the opening 123 at the first end 112 may have a diameter of about 3.5 mm, whereas the opening 121 at the second end 114 may have a diameter of about 4.1 mm. In other embodiments, the opening 123 at the first end 112 may have a diameter of about 3.5 mm, whereas the opening 121 at the second end 114 may have a diameter of about 5.5 mm. In other instances, the opening 123 at the first end 112 may have another diameter suitable for passing the reduced diameter portion 132 of the flexible cord 130 therethrough, yet not allowing the enlarged diameter portion 134 of the flexible cord 130 to pass through. With the diameter of the opening 121 sized larger than the diameter of the opening 123, the lumen 116 may taper from the diameter of the second opening 121 down to the diameter of the first opening 123.

Lumen 116 may further include one or more directional threads 118 or other retention structure, such as ridges, grooves, teeth, surface roughenings, etc., disposed adjacent to the reduced diameter 122 end. The threads 118 may be configured such that once cord 130 has been slid into the lumen 116, the cord 130 cannot be pulled in the opposite direction. For example, threads 118 may grip or "bite" into a portion of the cord 130 that has a larger diameter than the lumen 116, as will be discussed in more detail below. Lumen 116 may further include a threaded region 120 adjacent to the second end 114 of the connector 110 configured to receive a threaded rod 140 (see in FIG. 3).

In one embodiment, the flexible cord 130 may be formed from polyethylene-terephthalate (PET), although it will be recognized that various other materials suitable for implantation within the human body and for providing stabilization of the spine while maintaining flexibility may be used. In other embodiments, the flexible cord 130 can be constructed of other flexible materials such as metal, polymeric materials, or combinations of flexible materials. The flexible cord 130 may be of any length necessary to extend between two, three, four, or more vertebrae of the spinal column.

Flexible cord 130 may have an end portion 134 having a first diameter and a reduced diameter portion 132 having a second diameter extending from the end portion 134. The diameter of the reduced diameter portion 132 may be smaller than the diameter of the end portion 134. For example, in some instances, the diameter of the reduced diameter portion 132 may be smaller than the diameter of the lumen 116 while the end portion 134 may be larger than the diameter of at least a portion of the lumen 116. This may allow the reduced diameter portion 132 the flexible cord 130 to easily pass through the lumen 116 of the transition connector 110 and out the opening 123. In some instances the diameter of the end portion 134 may be substantially the same as or larger than an inner diameter or cross sectional dimension of the lumen 116.

The diameter of the opening 121 may be sized larger than the diameters of the reduced diameter portion 132 and the enlarged diameter end portion 134 of the cord 130, whereas the diameter of the opening 123 may be sized larger than the diameter of the reduced diameter portion 132 of the cord 130, but smaller than the diameter of the enlarged diameter end portion 134 of the cord 130.

Flexible cord 130 may further include a transition region 136 between reduced diameter portion 132 and end portion 134. Transition region 136 may provide a gradual transition from the first diameter to the second diameter in the form of a taper or, alternatively, transition region 136 may be a stepwise transition in which the reduced diameter portion 132 directly transitions into the end portion 134. However, it is contemplated that in some embodiments, flexible cord 130 may have a constant diameter over the length of the cord 130.

Figure 3:
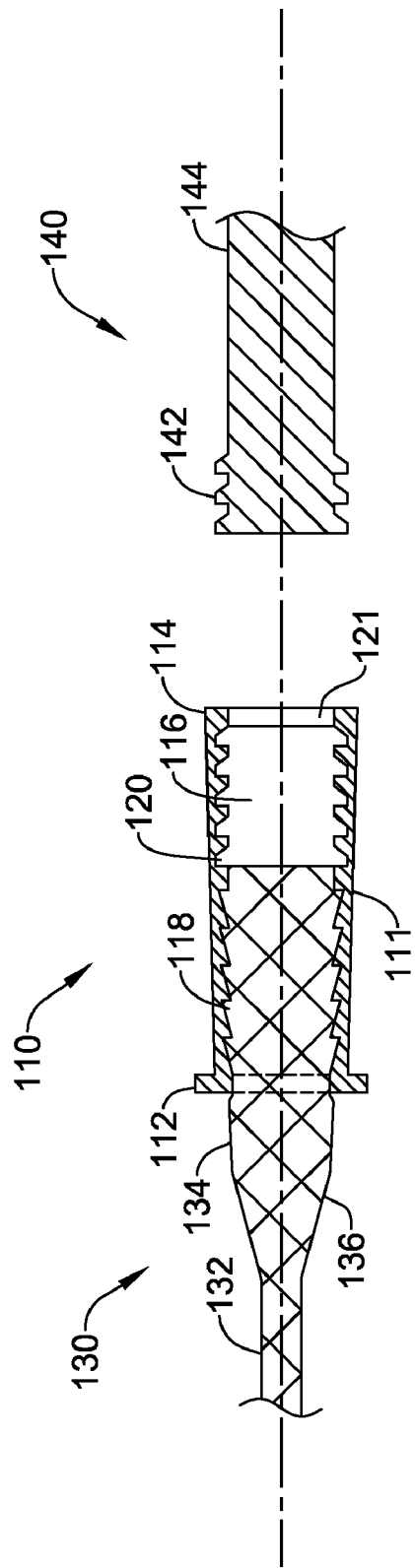
FIG. 3 is an axial cross-section of the transition connector and flexible member of FIG. 2 partially assembled.

In some embodiments, flexible cord 130 may be placed within the lumen 116 of the transition connector 110. For example, reduced diameter portion 132 of the cord 130 may be fed into the lumen 116 through opening 121 at the second (larger) end 114 of the connector 110. Reduced diameter portion 132 may be pulled through the lumen 116 such that it exits the lumen 116 through opening 123 at the first (smaller) end 112 of the connector 110. Thus, cord 130 may be pulled through the lumen 116 such that the reduced diameter portion 132 exits the lumen 116 while the end portion 134 remains within the lumen 116. A cord tensioner, or other such device, may be used to pull the cord 130 through the lumen 116. The cord 130 may be pulled until the end portion 134 engages the inner surface of the lumen 116 and/or the reduced diameter 122 portion adjacent the first end 112 of the connector 110. As the cord 130 is slid through the lumen 116, the end portion 134 of the cord 130 may be compressed against the inner surface of the lumen 116 and reduced diameter 122 of the first end 112 of the connector 110, as illustrated in FIG. 3. Retention features, such as threads 18 may engage the end portion 134 to help retain the end portion 134 in the lumen 116. As discussed above, threads 118 may be directional such that the cord 130 cannot be pulled out of the lumen 116 through the second (larger) end 114 of the connector 110.

FIG. 3 illustrates the enlarged diameter end portion 134 of a flexible cord 130 disposed in the lumen 116 of the connector 110 with a reduced diameter portion 132 of the cord 130 extending from the first end 112 of the connector 110. As discussed above, a threaded rigid rod 140 may be configured to mate with the threaded region 120 of the connector 110 such that the rigid rod 140 extends from the second end 114 of the connector 110. Rigid rod 140 may have a first threaded end 142 and a second unthreaded end 144. While rigid rod 140 is shown as having a circular cross section, the rigid rod 140 may have a cross section of any desired shape, including, but not limited to: square, rectangular, polygonal, or elliptical. The rigid rod 140 may be of any length necessary to extend between two, three, four, or more vertebrae of the spinal column.

Figure 3A:
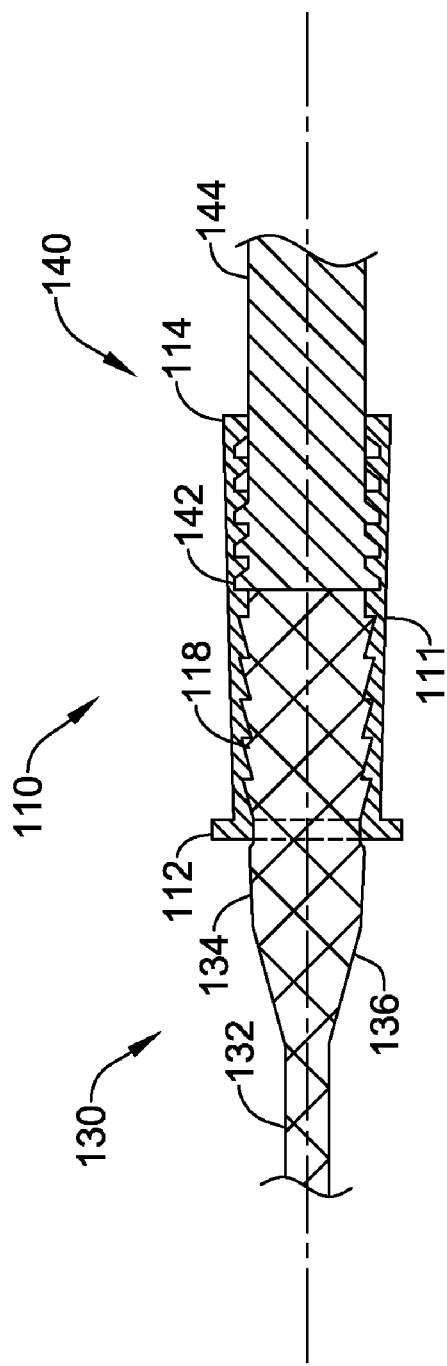
FIG. 3A is a cross-sectional view of the assembled transition connector of FIG. 3 coupled to a spinal rod.

As illustrated in FIG. 3A, when assembled, the transition connector 110 may connect a flexible cord 130 and a rigid rod 140 to allow for a rigid spinal stabilization system to transition to a more flexible spinal stabilization system. The transition connector 110 assembly may be used in conjunction with one or more vertebral fasteners as will be described in more detail below. As discussed above, the flexible cord 130 and/or the rigid rod 140 may be of any length necessary to extend between the desired number of vertebrae. The transition connector 110 may be formed from any biocompatible material, such as, but not limited to, titanium or stainless steel, or a suitable polymeric material.

Although not illustrated, the reduced diameter portion 132 of the flexible member such as the flexible cord 130 may extending through a spacer, as well as other components if desired. In some embodiments, the spacer may be an annular spacer having a lumen extending from a first end to a second end of the spacer. For example, in some embodiments the spacer may be a cylindrical member having a lumen extending therethrough. In some embodiments, the spacer may be formed from polycarbonate urethane (PCU), although it will be recognized that various other materials suitable for implantation within the human body and for providing stabilization of the spine while maintaining flexibility may be used. In other embodiments, the spacer can be constructed of other materials such as metal, polymeric materials, or combinations of materials.

Figure 3B:
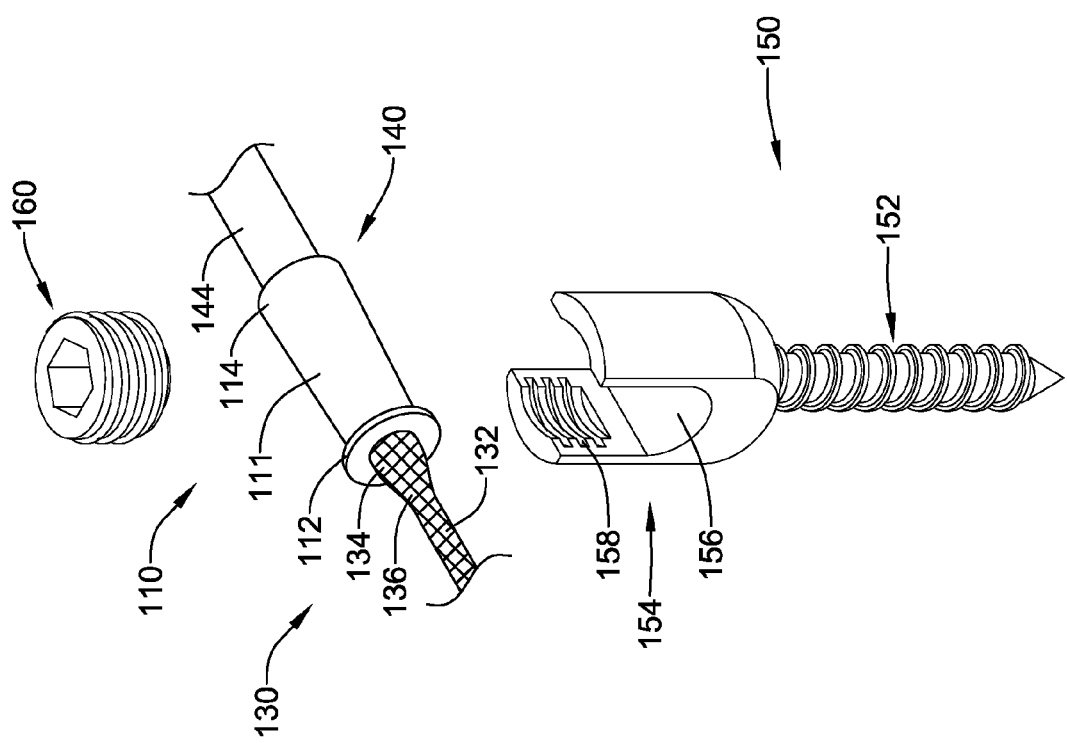
FIG. 3B is a exploded view of the assembled transition connector assembly of FIG. 3A with an illustrative bone screw.

FIG. 3B shows an exploded view of transition connector 110 with an illustrative vertebral fastener 150. The vertebral fasteners 150 may have a shank region 152, which in some embodiments may be a threaded region, for engaging a vertebra of the spinal column and a head portion 154, which in some embodiments may be an end region of the fastener 150 for receiving a stabilization device such as the transition connector 110, the rigid rod 144, or the flexible cord 130 of the vertebral stabilization system. In some embodiments, the head portion 154 of the fastener 150 may have a channel 156, such as a U-shaped channel, extending from a first side surface of the head portion 154 to a second side surface of the head portion 154 forming a saddle to receive a stabilization device. The head portion 154 may further include a threaded region 158 for threadably engaging a set screw 160, or other locking mechanism. One or more of the vertebral fasteners 150, may be designed such that the head portion 154 is movable relative to the shank portion 152 to be lockable in one of a plurality of angular positions (i.e., polyaxial), while one or more of the vertebral fasteners 150 may be configured such that the shank region 152 is fixedly attached to the head portion 154 (i.e., monoaxial), as desired.

Figure 3C:
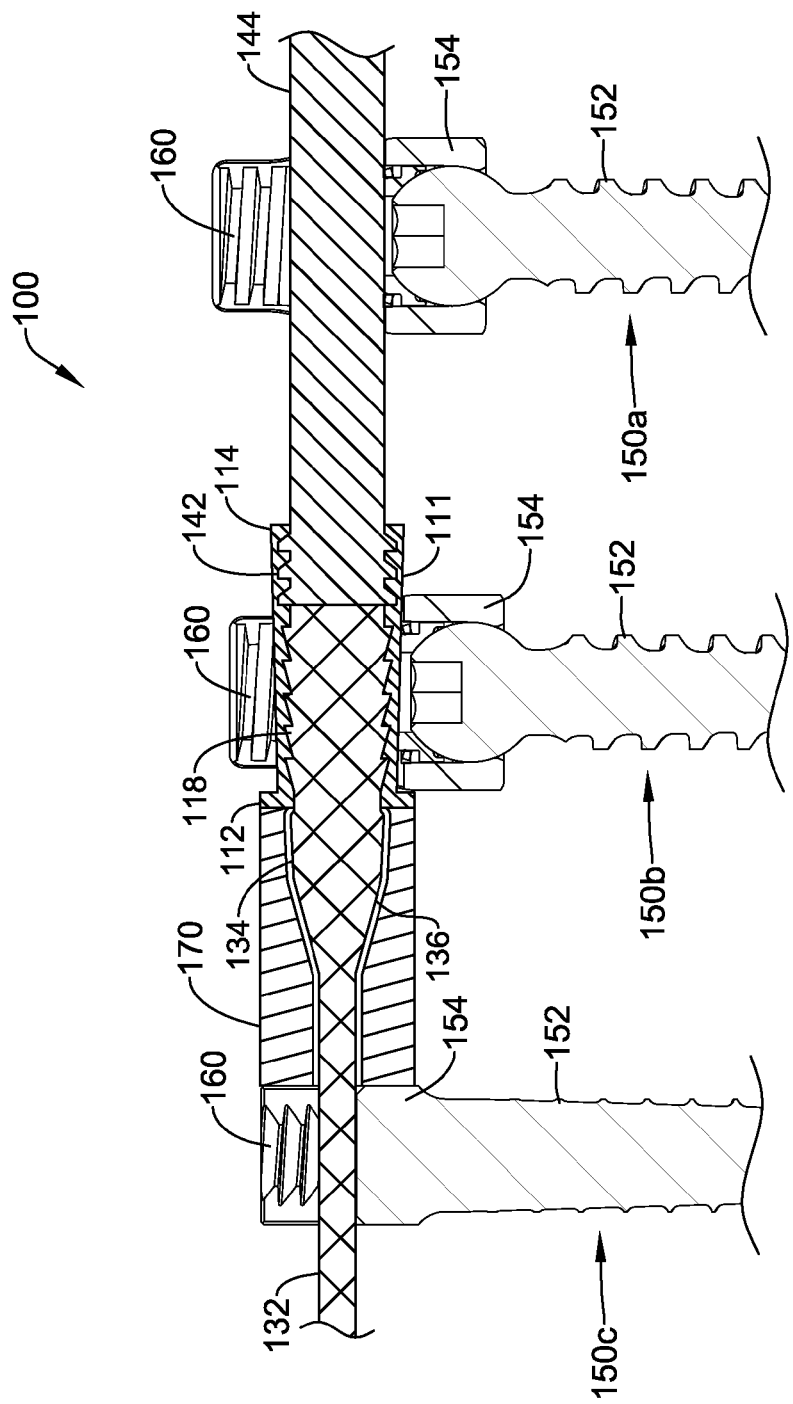
FIG. 3C is an axial cross-section of a vertebral stabilization system utilizing the illustrative transition connector of FIG. 3 coupled to a flexible cord.

As can be seen in FIG. 3C, the rigid tubular member 111 of the transition connector 110 may be disposed within the channel 156 of the fastener 150. First and second ends 112, 114 may be disposed on either side of the head portion 154 to help maintain the transition connector 110 from moving within the head portion 154. The transition connector 110 may be secured within the channel 156 by set screw 160. It is contemplated that transition connector 110 may span more than one vertebral fastener 150, if desired. For example, the transition connector 110 may be disposed in a fastener 150b such that rigid rod 144 extends from the transition connector 110 and is disposed within the channel 156 of a first fastener 150a and the flexible cord 130 extends from an opposite end of the transition connector 110 and is disposed within the channel 156 of a third fastener 150c. In some embodiments, the rigid rod portion 144 may have a length such that the rigid rod portion 144 spans a plurality of fasteners. It is contemplated that a variety of fasteners may be used within the vertebral support system 100. For example, one or more of the vertebral fasteners 150, may be designed such that the head portion 154 is movable relative to the shank portion 152 to be lockable in one of a plurality of angular positions (i.e., polyaxial), while one or more of the vertebral fasteners 150 may be configured such that the shank region 152 is fixedly attached to the head portion 154 (i.e., monoaxial), as desired.

As shown, the flexible cord 130 may extend out from the first end 112 of the transition connector 110 towards a third fastener 150c. A second portion of the flexible cord 130 may be disposed within a channel 156 of the third fastener 150c. The flexible cord 130 may be secured within the channel of the third fastener 150c by a set screw 160 or other locking means. In some embodiments, the flexible cord 130 may be sized such that it spans a plurality of fasteners (not explicitly shown).

A flexible spacer 170 may be disposed about the flexible cord 130 and disposed between a second side of the head portion 154 of the second fastener 150b and a first side of the head portion 154 of the third fastener 150c. In some embodiments, the flexible spacer 170 may include a central lumen through which the flexible cord 130 extends. In some embodiments, the flexible spacer may be formed from polycarbonate urethane (PCU), although it will be recognized that various other materials suitable for implantation within the human body and for providing stabilization of the spine while maintaining flexibility may be used. In other embodiments, the flexible spacer can be constructed of other flexible materials such as metal, polymeric materials, or combinations of flexible materials.

Figure 4:
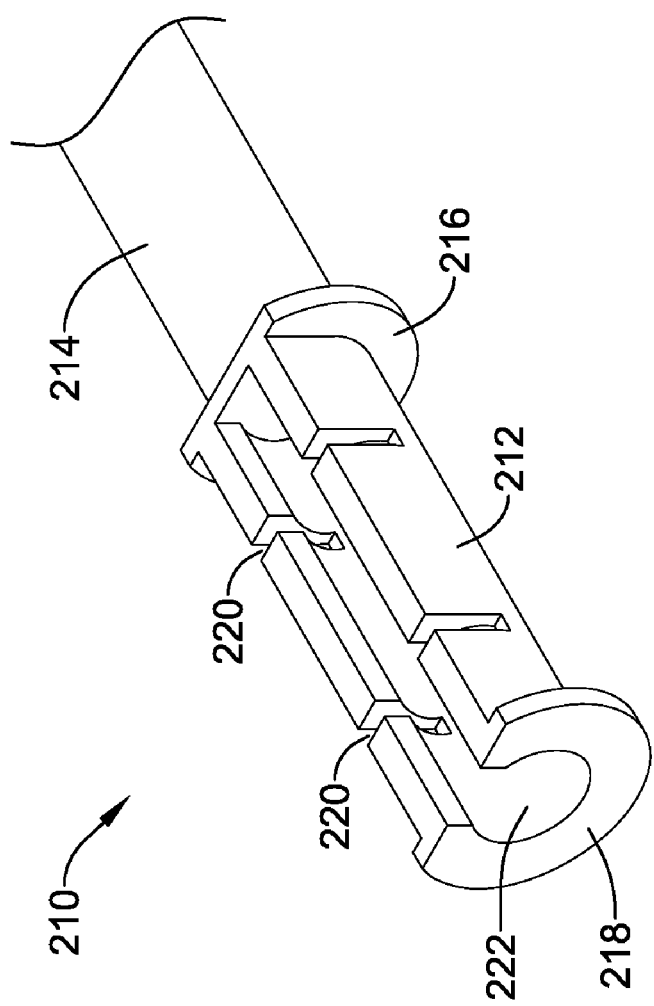
FIG. 4 is a perspective view of another illustrative transition connector.

FIG. 4 is a perspective view of another illustrative transition connector 210 for connecting a rigid rod construct and a flexible construct, to control relative motion of adjacent vertebrae along a region of a spinal column with a plurality of fasteners, such as bone screws. The transition connector 210 may include a first portion 212 and a second portion 214. First portion 212 may include a first end 218 and a second end 216. In some instances, the first and second ends 218, 216 of the first portion 212 may include flange portions such that ends 218, 216 have an enlarged diameter relative to a middle portion of the first portion 212. In some instances, the flange portions of ends 218, 216, may help retain transition connector 210 within the channel of a housing of a pedicle screw or other fixation device. In some embodiments, the first portion 212 may have a uniform cross-sectional diameter along the length of the first portion 212. The first portion 212 of the transition connector 210 is shown as having a generally U-shaped cross section, however, the transition connector 210 may have a cross section of any desired shape.

First portion 212 may further include an open channel 222, such as a C-shaped channel or a U-shaped channel, extending from the first end 218 to the second end 216. In some instances, at least a portion of the channel 222 may be shaped to receive the end portion of a flexible cord 230 (see FIG. 4A) or other flexible member therein. First portion 212 may further include one or more grooves or slots 220 disposed in a sidewall of channel 222 for receiving one or more pins 232, as discussed in more detail with respect to FIG. 4A. The slots 220 may be sized and shaped to receive any shape pin desired.

Second portion 214 may include a rigid rod structure. While rigid rod 214 is shown as having a circular cross section, the rigid rod 214 may have a cross section of any desired shape, including, but not limited to: square, rectangular, polygonal, or elliptical. The rigid rod 214 may be of any length necessary to extend between two, three, four, or more vertebrae of the spinal column. In some embodiments, rigid rod 214 may form a unitary structure with first portion 212. In other embodiments, rigid rod 214 may be formed separately and attached to the first portion 212 by any means desired, such as, but not limited to: welding, brazing, soldering, or adhesive.

FIG. 4A shows an illustrative flexible cord 230 for use with transition connector 210. In one embodiment, the flexible cord 230 may be formed from polyethylene-terephthalate (PET), although it will be recognized that various other materials suitable for implantation within the human body and for providing stabilization of the spine while maintaining flexibility may be used. In other embodiments, the flexible cord 230 can be constructed of other flexible materials such as metal, polymeric materials, or combinations of flexible materials. The flexible cord 230 may be of any length necessary to extend between two, three, four, or more vertebrae of the spinal column. In some instances, the cord 230 may include one or more pins 232 extending radially from the cord 230. Pins 232 may generally extend entirely through the diameter of the cord 230 such that a first end portion and a second end portion protrude radially from the cord 230 on opposite sides of the cord 230. End portions of pins 232 may be sized and shaped to mate with corresponding grooves 220 on the first portion 212 of the transition connector 210. While pins 232 are shown as having a circular cross section, the pins 232 may have a cross section of any desired shape, including, but not limited to: square, rectangular, polygonal, or elliptical.

Figure 5:
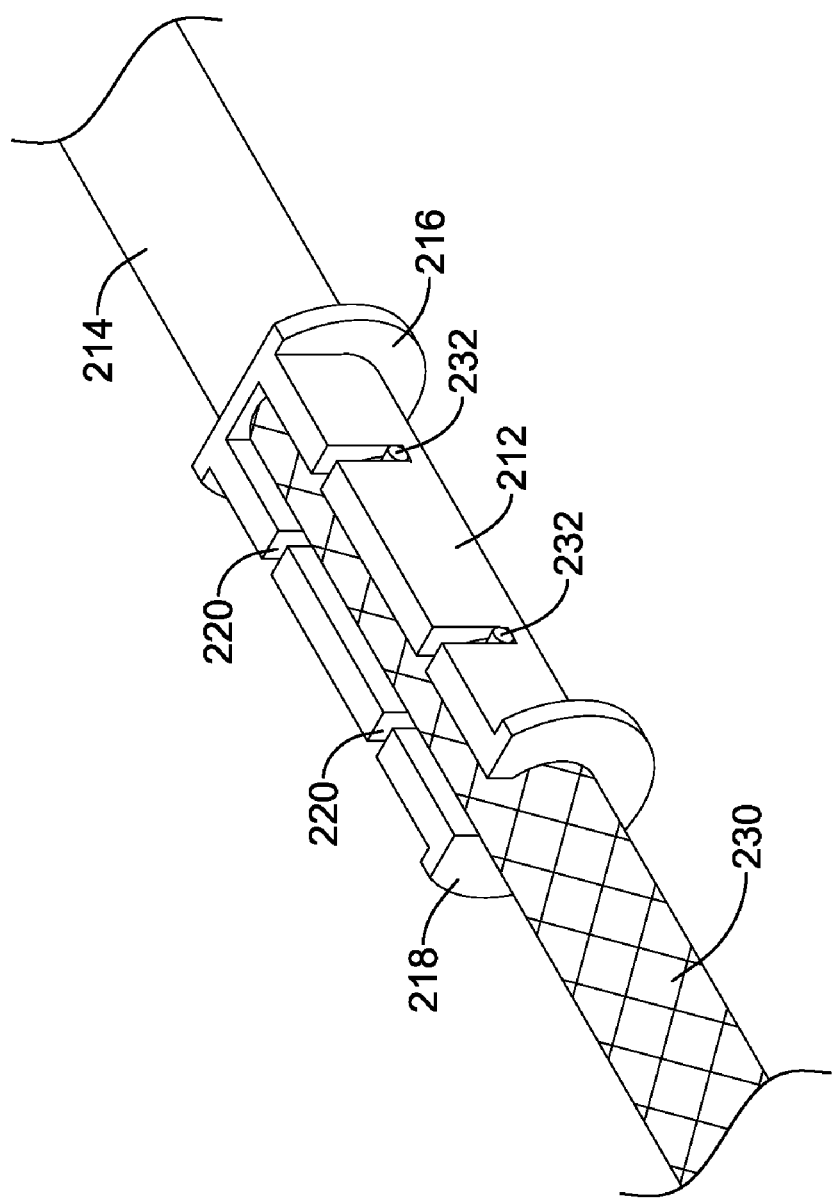
FIG. 5 is a perspective view of the assembled transition connector and flexible member of FIGS. 4 and 4A.

As illustrated in FIG. 5, when assembled, the transition connector 210 may connect a flexible cord 230 and a rigid rod 214 to allow for a rigid spinal stabilization system to transition to a more flexible spinal stabilization system. The transition connector 210 assembly may be used in conjunction with one or more vertebral fasteners, such as bone screws, as will be described in more detail below. As discussed above, the flexible cord 230 and/or the rigid rod 214 may be of any length necessary to extend between the desired number of vertebrae. The transition connector 210 may be formed from any biocompatible material, such as, but not limited to, titanium or stainless steel, or a suitable polymeric material. Cord 230 may be top-loaded into channel 222 of the transition connector 210 such that the end portions of pins 232 align and are disposed within grooves 220 on opposing sides of the channel 222. Pins 232 may prevent the cord 230 from sliding out of the channel 222 in a direction along the longitudinal axis of the cord 230.

In some instances, the grooves or slots 220 may be perpendicular to the longitudinal axis of the cord 230, while in other embodiments the grooves or slots 220 may be angled at an oblique angle to the longitudinal axis of the cord 230.

Figure 5A:
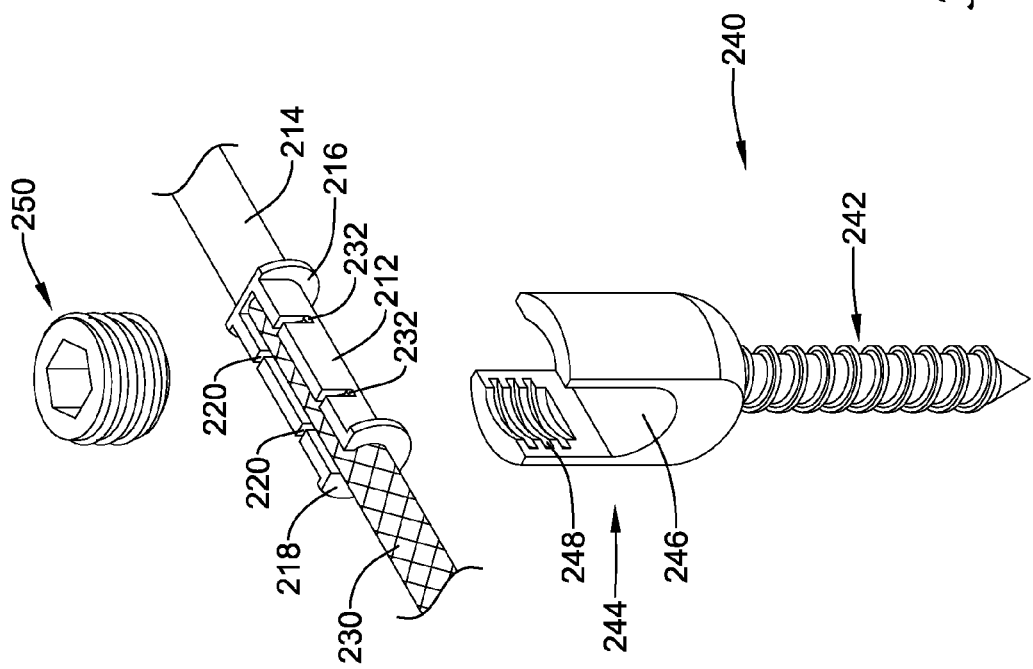
FIG. 5A is an exploded view of the assembled transition connector assembly of FIG. 5 with an illustrative bone screw.

FIG. 5A shows an exploded view of transition connector 210 with an illustrative vertebral fastener 240. The vertebral fasteners 240 may have a shank region 242, which in some embodiments may be a threaded region, for engaging a vertebra of the spinal column and a head portion 244, which in some embodiments may be an end region of the fastener 240 for receiving a stabilization device such as the transition connector 210, the rigid rod 214, or the flexible cord 230 of the vertebral stabilization system. In some embodiments, the head portion 244 of the fastener 240 may have a channel 246, such as a U-shaped channel, extending from a first side surface of the head portion 244 to a second side surface of the head portion 244 forming a saddle to receive a stabilization device. The head portion 244 may further include a threaded region 248 for threadably engaging a set screw 250, or other locking mechanism. One or more of the vertebral fasteners 240, may be designed such that the head portion 244 is movable relative to the shank portion 242 to be lockable in one of a plurality of angular positions (i.e., polyaxial), while one or more of the vertebral fasteners 240 may be configured such that the shank region 242 is fixedly attached to the head portion 244 (i.e., monoaxial), as desired.

Figure 5B:
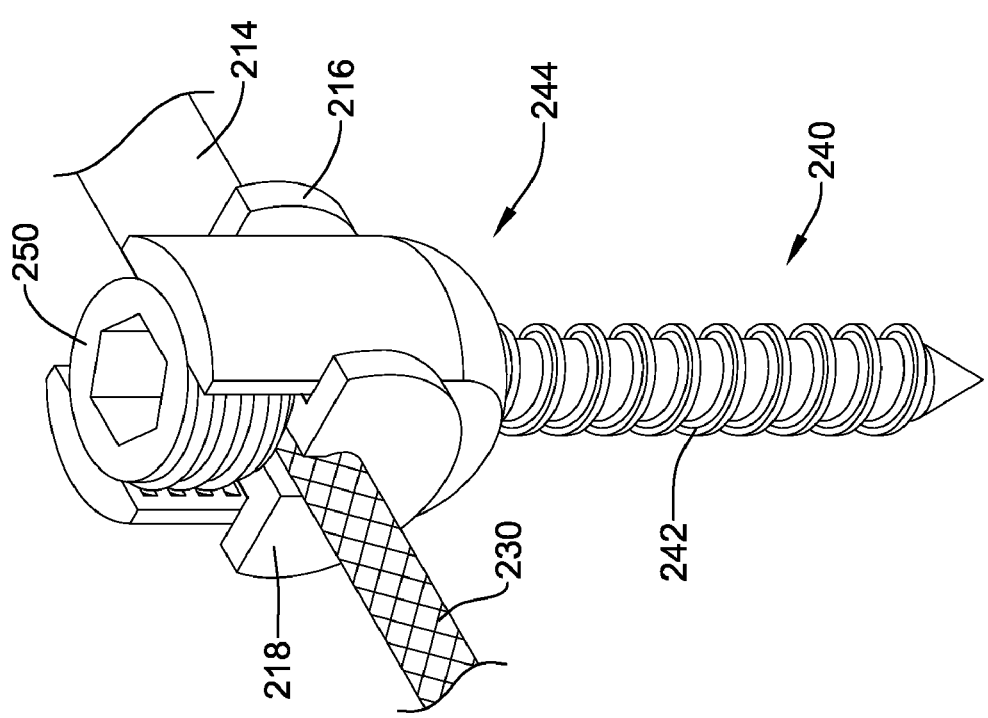
FIG. 5B is a perspective view of the assembled transition connector assembly of FIG. 5 secured with an illustrative bone screw.

As can be seen in FIG. 5B, the first portion 212 of the transition connector 210 may be disposed within the channel 246 of the fastener 240. First and second ends 218, 216 may be disposed on either side of the head portion 244 to help maintain the transition connector 210 from moving within the head portion 244. The transition connector 210 may be secured within the channel 246 by set screw 250. Set screw 250 may further prevent the cord 230 from exiting the top of the channel 222 of the first portion 212. It is contemplated that transition connector 210 may span more than one vertebral fastener 240, if desired. For example, the transition connector 210 may span between first and second fasteners such that rigid rod 214 is disposed within the channel 246 of a first fastener (not explicitly shown) and first portion 212 is disposed within the channel 246 of a second fastener 240. In some embodiments, the rigid rod portion 214 may have a length such that the rigid rod portion 214 spans a plurality of fasteners (not explicitly shown).

The flexible cord 230 may extend out from the first portion 212 of the transition connector 210 towards a third fastener (not explicitly shown). A second portion of the flexible cord 230 may be disposed within a channel of the third fastener. The flexible cord 230 may be secured within the channel of the third fastener by a set screw or other locking means. In some embodiments, the flexible cord 230 may be sized such that it spans a plurality of fasteners (not explicitly shown).

A flexible spacer (not explicitly shown) may be disposed about the flexible cord 230 and disposed between a second side of the head portion 244 of the second fastener 240 and a first side of the head portion of the third fastener. In some embodiments, the flexible spacer may include a central lumen through which the flexible cord 230 extends. In some embodiments, the flexible spacer may be formed from polycarbonate urethane (PCU), although it will be recognized that various other materials suitable for implantation within the human body and for providing stabilization of the spine while maintaining flexibility may be used. In other embodiments, the flexible spacer can be constructed of other flexible materials such as metal, polymeric materials, or combinations of flexible materials.

While not explicitly shown, it is contemplated that any of the transition connectors described may be secured within vertebral fasteners in a similar manner to that discussed with respect to FIGS. 3B, 3C, and 5A.

Figure 6:
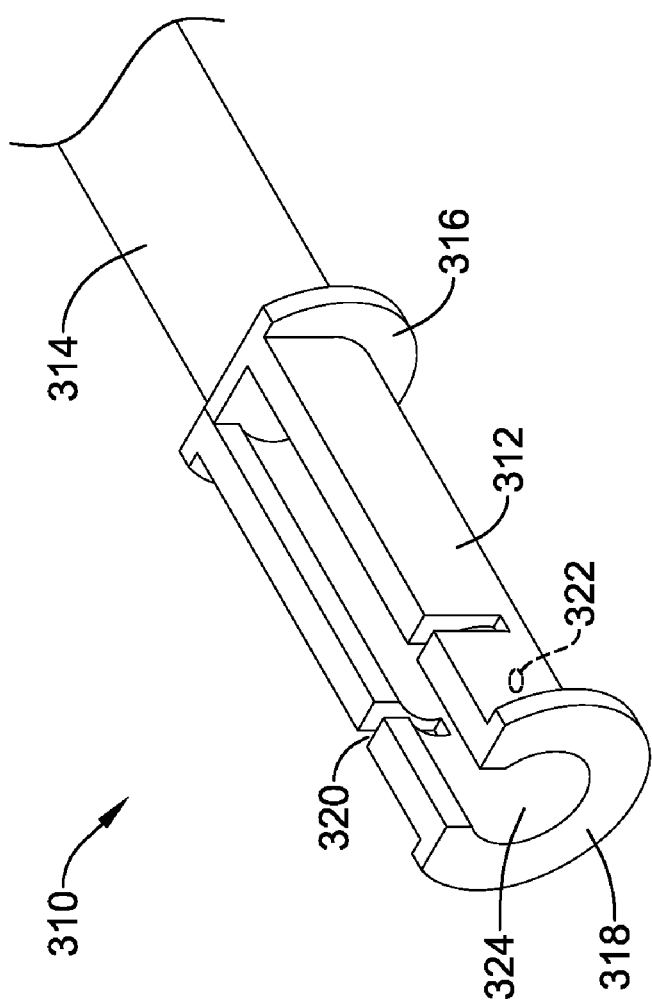
FIG. 6 is a perspective view of another illustrative transition connector.

FIG. 6 is a perspective view of another illustrative transition connector 310 for connecting a rigid rod construct and a flexible construct, to control relative motion of adjacent vertebrae along a region of a spinal column with a plurality of fasteners, such as bone screws. The transition connector 310 may include a first portion 312 and a second portion 314. First portion 312 may include a first end 318 and a second end 316. In some instances, the first and second ends 318, 316 of the first portion 312 may include flange portions such that ends 318, 316 have an enlarged diameter portion relative to a middle portion of the first portion 312. In some instances, the flange portions of ends 318, 316, may help retain transition connector 310 within the channel of a housing of a pedicle screw or other fixation device. In some embodiments, the first portion 312 may have a uniform cross-sectional diameter along the length of the first portion 312. The first portion 312 of the transition connector 310 is shown as having a generally U-shaped cross section, however, the transition connector 310 may have a cross section of any desired shape.

First portion 312 may further include an open channel 324, such as a C-shaped channel or a U-shaped channel, extending from the first end 318 to the second end 316. In some instances, at least a portion of the channel 324 may shaped to receive the end portion of a flexible cord 330 (see FIG. 6A) or other flexible member. First portion 312 may further include one or more grooves or slots 320 disposed in a sidewall of channel 324 for receiving one or more pins 332, as discussed in more detail with respect to FIG. 6A. The slots 320 may be sized and shaped to receive any shape pin desired. In some embodiments, first portion 312 may include one or more holes 322 disposed in the bottom of channel 324 for receiving one or more pins 334 extending radially from the cord 330, as discussed in more detail with respect to FIG. 6A. Pins 332 may extend entirely through the diameter of the cord 330 in a first direction while pins 334 may extend entirely through the diameter of the cord in a second direction generally perpendicular to the first direction. While slots 320 and hole 322 are shown as generally aligned, it is contemplated that in some embodiments, slots 320 and hole 322 may be longitudinally offset from one another.

Second portion 314 may include a rigid rod structure. While rigid rod 314 is shown as having a circular cross section, the rigid rod 314 may have a cross section of any desired shape, including, but not limited to: square, rectangular, polygonal, or elliptical. The rigid rod 314 may be of any length necessary to extend between two, three, four, or more vertebrae of the spinal column. In some embodiments, rigid rod 314 may form a unitary structure with first portion 312. In other embodiments, rigid rod 314 may be formed separately and attached to the first portion 312 by any means desired, such as, but not limited to: welding, brazing, soldering, or adhesive.

FIG. 6A shows an illustrative flexible cord 330 for use with transition connector 310. In one embodiment, the flexible cord 330 may be formed from polyethylene-terephthalate (PET), although it will be recognized that various other materials suitable for implantation within the human body and for providing stabilization of the spine while maintaining flexibility may be used. In other embodiments, the flexible cord 330 can be constructed of other flexible materials such as metal, polymeric materials, or combinations of flexible materials. The flexible cord 330 may be of any length necessary to extend between two, three, four, or more vertebrae of the spinal column. In some instances, the cord 330 include one or more pins 332, 334 extending radially from the cord 330 such that a first end portion and a second end portion of the pins 332, 334 protrude radially from the cord 330 on opposite sides of the cord 330. Pins 332, 334 may be sized and shaped such that the end portions may mate with corresponding grooves 320 and/or holes 322 on the first portion 312 of the transition connector 310. While pins 332, 334 are shown as having a circular cross section, the pins 332, 334 may have a cross section of any desired shape, including, but not limited to: square, rectangular, polygonal, or elliptical.

Figure 7:
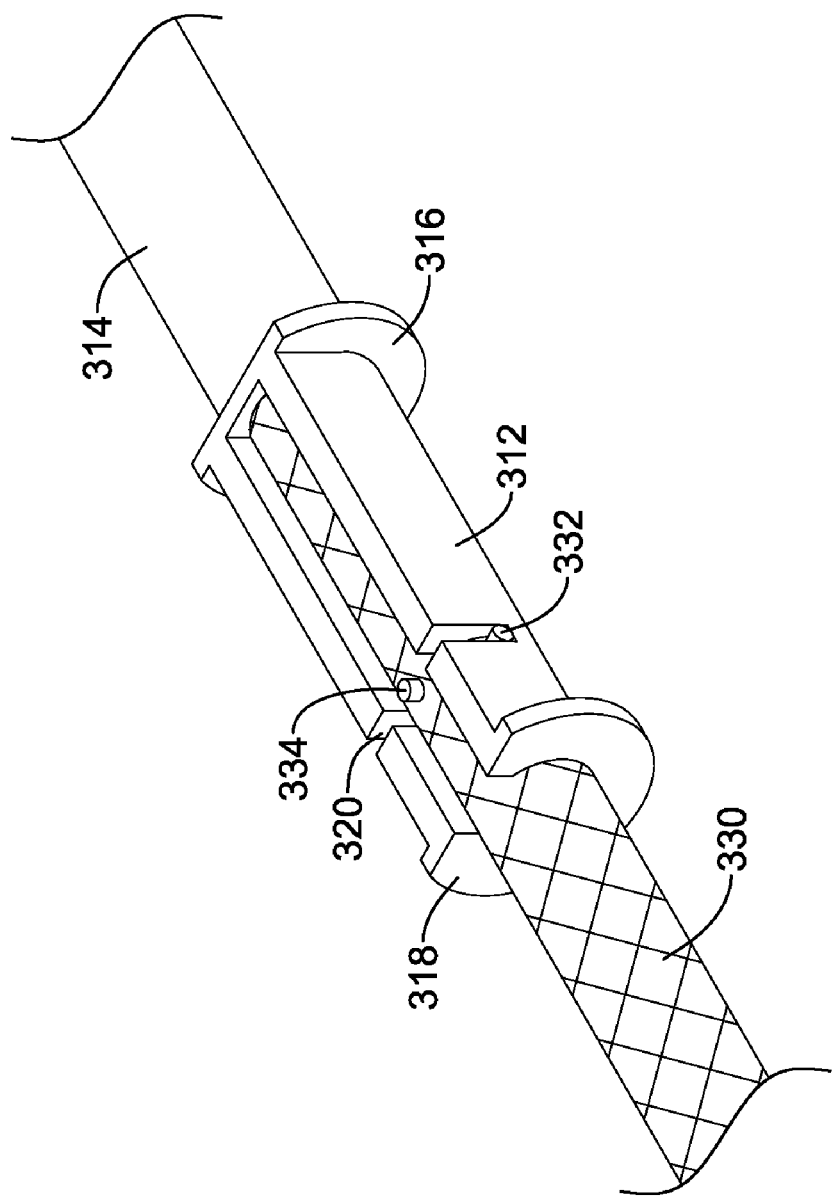
FIG. 7 is a perspective view of the assembled transition connector and flexible member of FIGS. 6 and 6A.

As illustrated in FIG. 7 when assembled, the transition connector 310 may connect a flexible cord 330 and a rigid rod 314 to allow for a rigid spinal stabilization system to transition to a more flexible spinal stabilization system. The transition connector 310 assembly may be used in conjunction with one or more vertebral fasteners, such as bone screws, as described above with respect of FIGS. 5A and 5B. As discussed above, the flexible cord 330 and/or the rigid rod 314 may be of any length necessary to extend between the desired number of vertebrae. The transition connector 310 may be formed from any biocompatible material, such as, but not limited to, titanium or stainless steel. Cord 330 may be top-loaded into channel 324 of the transition connector 310 such that the end portions of pins 332, 334 align and are disposed within grooves 320 on opposing sides of the channel 324 and/or hole 322. Pins 332, 334 may prevent the cord 330 from sliding out of the channel 324 in a direction along the longitudinal axis of the cord 330.

Figure 8:
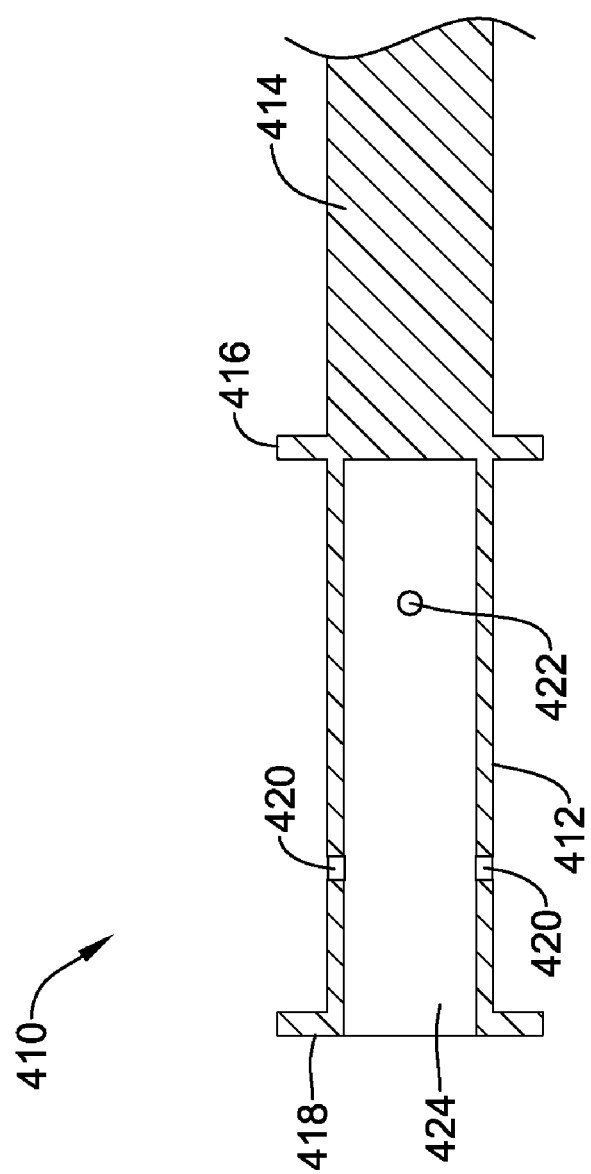
FIG. 8 is a top view of another illustrative transition connector.

FIG. 8 is a cross-sectional view of another illustrative transition connector 410 for connecting a rigid rod construct and a flexible construct, to control relative motion of adjacent vertebrae along a region of a spinal column with a plurality of fasteners, such as bone screws. The transition connector 410 may include a first portion 412 and a second portion 414. First portion 412 may include a first end 418 and a second end 416. In some instances, the first and second ends 418, 416 of the first portion 412 may include flange portions such that ends 418, 416 have an enlarged diameter portion relative to a middle portion of the first portion 412, In some instances, the flange portions of ends 418, 416, may help retain transition connector 410 within the channel of a housing of a pedicle screw or other fixation device. In some embodiments, the first portion 412 may have a uniform cross-sectional diameter along the length of the first portion 412.

First portion 412 may further include an open channel 424, such as a C-shaped channel or a U-shaped channel, extending from the first end 418 to the second end 416. However, the channel 424 may have any desired cross sectional shape. In some instances, at least a portion of the channel 424 may be shaped to receive the end portion of a flexible cord or other flexible member. First portion 412 may further include one or more grooves or slots 420 disposed in a sidewall of channel 424 for receiving one or more horizontal pins extending through the flexible cord. The slots 420 may be sized and shaped to receive any shape pin desired. In some embodiments, first portion 412 may include one or more holes 422 disposed in the bottom of channel 324 for receiving one or more vertical pins extending through the flexible cord. In some instances, the hole(s) 422 may be offset from the slots 420, however, in other embodiments the hole(s) 422 may be aligned with the slots 420. Horizontal pins may extend through the diameter of the cord in a first direction while vertical pins may extend through the diameter of the cord in a second direction generally perpendicular to the first direction. Horizontal pins may be disposed in the slots 420 while vertical pins may be disposed in the holes 422. While slots 420 and hole 422 are shown as offset, it is contemplated that in some embodiments, slots 420 and hole 422 may be generally aligned with one another.

Second portion 414 may include a rigid rod structure. While rigid rod 414 is shown as having a circular cross section, the rigid rod 414 may have a cross section of any desired shape, including, but not limited to: square, rectangular, polygonal, or elliptical. The rigid rod 414 may be of any length necessary to extend between two, three, four, or more vertebrae of the spinal column. In some embodiments, rigid rod 414 may form a unitary structure with first portion 412. In other embodiments, rigid rod 414 may be formed separately and attached to the first portion 412 by any means desired, such as, but not limited to: welding, brazing, soldering, or adhesive.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A vertebral stabilization system comprising:
   a flexible member having an end portion and a reduced diameter portion extending from the end portion;

a transition connector having a first end and a second end and defining a lumen extending from the first end to the second end, the lumen configured to receive the end portion of the flexible member with the reduced diameter portion extending from the first end of the transition connector;

a rigid rod extending within the lumen at the second end of the transition connector; and a first vertebral anchor including a head portion and a shank extending from the head portion, the head portion of the first vertebral anchor including a channel extending from a first side surface of the head portion to a second side surface of the head portion;

wherein the transition connector is positionable in the channel of the head portion of the first vertebral anchor;

wherein when the end portion of the flexible member is disposed in the lumen, the reduced diameter portion of the flexible member extends from the first end of the transition connector; and wherein the lumen transitions from a first diameter at the first end to a second diameter at the second end, the first diameter being smaller from the second diameter.

2. The vertebral stabilization system of claim 1, wherein the end portion of the flexible member has a first diameter and the reduced diameter portion has a second diameter less than the first diameter.

3. The vertebral stabilization system of claim 2, wherein the first diameter of the end portion of the flexible member is greater than the first diameter of the lumen proximate the first end of the transition member such that the end portion cannot pass through the first end of the transition connector.

4. The vertebral stabilization system of claim 1, wherein a first end of the lumen includes directional threads configured to engage the end portion of the flexible member.

5. The vertebral stabilization system of claim 1, wherein a second end of the lumen includes a threaded region.

6. The vertebral stabilization system of claim 5, wherein the rigid rod includes a threaded end configured to threadably engage the threaded region of the lumen of the transition connector.

7. The vertebral stabilization system of claim 1, further comprising:

a first vertebral anchor including a head portion having a channel extending therethrough;

a second vertebral anchor including a head portion having a channel extending therethrough; and a third vertebral anchor including a head portion having a channel extending therethrough;

wherein the transition connector is positionable in the channel of the head portion of the first vertebral anchor while the rigid rod extends from the transition connector and is positioned in the channel of the head portion of the second vertebral anchor and the flexible member extends from the transition connector and is positioned in the channel of the head portion of the third vertebral anchor.

8. The vertebral stabilization system of claim 7, wherein the flexible member extends through a spacer positioned between the head portion of the first vertebral anchor and the head portion of the third vertebral anchor.

9. A vertebral stabilization system comprising:

a flexible member including an end portion having a first diameter and a reduced diameter portion extending from the end portion, the reduced diameter portion having a second diameter;

a transition connector having a first end, a second end, and a lumen extending completely therethrough configured to receive the end portion of the flexible member, the lumen tapering from a larger diameter at the second end to a smaller diameter at the first end;

a rigid rod extending within the lumen at the second end of the transition connector; and a first vertebral anchor including a head portion and a shank extending from the head portion, the head portion of the first vertebral anchor including a channel extending from a first side surface of the head portion to a second side surface of the head portion;

wherein when the end portion of the flexible member is disposed in the lumen, the reduced diameter portion of the flexible member extends from the first end of the transition connector; and wherein the transition connector is positionable in the channel of the head portion of the first vertebral anchor.

10. The vertebral stabilization system of claim 9, wherein the first diameter of the end portion of the flexible member is greater than a diameter of the lumen proximate the first end of the transition connector such that the end portion cannot pass through the first end.

11. The vertebral stabilization system of claim 10, wherein the larger diameter of the lumen is greater than the first diameter of the end portion of the flexible member.

12. The vertebral stabilization system of claim 9, wherein the rigid rod includes a first threaded region and a second unthreaded region, the first threaded region configured to threadably engage a threaded region of the transition connector.

13. The vertebral stabilization system of claim 9, further comprising:

a first vertebral anchor including a head portion having a channel extending therethrough;

a second vertebral anchor including a head portion having a channel extending therethrough; and a third vertebral anchor including a head portion having a channel extending therethrough;

wherein the transition connector is positionable in the channel of the head portion of the first vertebral anchor while the rigid rod extends from the second end of the transition connector and is positioned in the channel of the head portion of the second vertebral anchor and the flexible member extends from the first end of the transition connector and is positioned in the channel of the head portion of the third vertebral anchor.

14. The vertebral stabilization system of claim 9, wherein a first end of the lumen includes directional threads configured to engage the flexible member.

15. The vertebral stabilization system of claim 9, wherein the flexible member is a cord.

* * * * *